US010646250B2

(12) United States Patent
Mohajer-Shojaee

(10) Patent No.: US 10,646,250 B2
(45) Date of Patent: May 12, 2020

(54) TROCAR ASSEMBLIES WITH MOVABLE ATRAUMATIC TIP AND METHODS FOR USE

(71) Applicant: Reza Mohajer-Shojaee, Encino, CA (US)

(72) Inventor: Reza Mohajer-Shojaee, Encino, CA (US)

( * ) Notice: Subject to any disclaimer, the term of this patent is extended or adjusted under 35 U.S.C. 154(b) by 363 days.

(21) Appl. No.: 15/653,903

(22) Filed: Jul. 19, 2017

(65) Prior Publication Data

US 2018/0021057 A1 Jan. 25, 2018

Related U.S. Application Data

(60) Provisional application No. 62/364,132, filed on Jul. 19, 2016.

(51) Int. Cl.
| | |
|---|---|
| *A61B 17/34* | (2006.01) |
| *A61B 90/00* | (2016.01) |
| *A61B 90/30* | (2016.01) |
| *A61B 17/00* | (2006.01) |

(52) U.S. Cl.
CPC ...... *A61B 17/3421* (2013.01); *A61B 17/3496* (2013.01); *A61B 17/3474* (2013.01);
(Continued)

(58) Field of Classification Search
CPC ........ A61B 17/3496; A61B 2090/3945; A61B 90/30; A61B 2017/00907
See application file for complete search history.

(56) References Cited

U.S. PATENT DOCUMENTS

| 4,535,773 A | 8/1985 | Yoom |
|---|---|---|
| 4,654,030 A | 3/1987 | Moll et al. |
| (Continued) | | |

FOREIGN PATENT DOCUMENTS

| CN | 1638835 | 7/2005 |
|---|---|---|
| RU | 109399 | 10/2011 |

OTHER PUBLICATIONS

Fuller, Janie, et al, Laparoscopic Trocar Injuries: A report from U.S. Food and Drug Administration (FDA) Center for Devices and Radiological Health (CDRH) Systematic Technology Assessment of Medical Products (STAMP) Committee: FDA Safety Communication; Finalized Nov. 7, 2003.
(Continued)

*Primary Examiner* — Anh T Dang
(74) *Attorney, Agent, or Firm* — Dinsmore & Shohl LLP

(57) ABSTRACT

Trocar assemblies and methods of use in minimally invasive surgical procedures are described. Such trocar assemblies include a head, a distally extending shaft including an open distal end, a cutting component extending through the open distal end, and a retractable protection assembly to extend and retract through the open distal end of the shaft. The retractable protection assembly extends through the open distal end to cover the cutting component in a naturally biased position. Further, the retractable protection assembly retracts from the open distal end to expose the cutting component in a compressed position during application of body pressure to the retractable protection assembly until reaching a body cavity. Upon reaching the body cavity and removal of body pressure, the retractable protection assembly returns to the naturally biased position and extends through the open distal end to cover the cutting component.

19 Claims, 6 Drawing Sheets

(52) U.S. Cl.
CPC ..... *A61B 90/30* (2016.02); *A61B 2017/00907* (2013.01); *A61B 2017/3456* (2013.01); *A61B 2090/0811* (2016.02); *A61B 2090/3945* (2016.02)

(56) References Cited

U.S. PATENT DOCUMENTS

| | | | |
|---|---|---|---|
| 5,256,149 A | | 10/1993 | Banik et al. |
| 5,295,977 A | * | 3/1994 | Cohen ............... A61M 25/0606 604/164.12 |
| 5,387,197 A | | 2/1995 | Smith et al. |
| 5,423,796 A | | 6/1995 | Shikhman et al. |
| 5,797,943 A | | 8/1998 | Danks et al. |
| 6,238,407 B1 | | 5/2001 | Wolf et al. |
| 8,029,474 B2 | | 10/2011 | Chung |
| 8,523,817 B2 | | 9/2013 | Mohajer |
| 8,838,206 B2 | * | 9/2014 | Mohajer ............ A61B 17/3474 600/424 |
| 9,579,472 B2 | | 2/2017 | Mohajer-Shojaee |
| 2013/0274776 A1 | | 10/2013 | Begg |
| 2013/0331657 A1 | * | 12/2013 | Basson ................. A61B 90/30 600/249 |

OTHER PUBLICATIONS

The Emergency Care Research Institute (ECRI); Trocars: Safety and Selection. 1998;27;376-98; Dated Nov. 1998, vol. 27. No. 11.

Rhodes, R., Laparoscopic Trocar Complications, Prevention & Management of Laparoendoscopic Surgical Complications, 3rd Ed., available at http://laparoscopy.blogs.com/prevention_management_3/2010/11/laparoscopic-trocar-complications.html.

Fanning, J. & Shah, M. & Fenton, B. Reduced-Force Closed Trocar Entry Technique: Analysis of Trocar Insertion Force Using a Mechanical Force Gauge, Journal of the Society of Laparoscopic Surgeons, Jan-Mar., 15(1), 59-61 (2011), available at https://www.ncbi.nlm.nih.gov/pmc/articles/PMC3134697/.

International Search Report and Written Opinion dated Oct. 12, 2017 in International Application No. PCT/US2017/042814.

International Preliminary Report on Patentability relating to International Application No. PCT/US2017/042814 dated Jan. 31, 2019.

Vilos GA et al., Laparoscopic Entry: A Review of Techniques, Technologies, and Complications, The Society of Obstetricians and Gynaecologists of Canada in its SOGC Clinical Practice Guideline, No. 193, May 2007, available at https://www.ncbi.nlm.nih.gov/pubmed/17493376.

Fanning J et al., Reduced-Force Closed Trocar Entry Technique: Analysis of Trocar Insertion Force Using a Mechanical Force Gauge, Journal of the Society of Laparoendoscopic Surgeons. JSLS (2011)15:59-61, PMC3134697, PMID: 21902944, doi: 10.4293/108680811X13022985131219), available at https://www.ncbi.nlm.nih.gov/pmc/articles/PMC3134697/.

Ben Mazur, Slow motion shielded trocar injury analysis, YouTube, published on Jun. 11, 2018, available at https://www.youtube.com/watch?v=20asOdG6XHk.

* cited by examiner

TROCAR ASSEMBLIES WITH MOVABLE ATRAUMATIC TIP AND METHODS FOR USE

CROSS REFERENCE TO RELATED APPLICATIONS

The present specification claims priority to U.S. Provisional Patent Application Ser. No. 62/364,132, filed Jul. 19, 2016, the entirety of which is incorporated by reference herein.

TECHNICAL FIELD

The present disclosure generally relates to surgical instruments and, more specifically, to trocar assemblies as surgical instruments and methods of use to penetrate body tissue.

BACKGROUND

Minimally invasive surgical procedures are becoming more desirable as a surgical method of choice due to advantages provided when compared to traditional open surgery such as a higher surgical accuracy rate, less tissue damage, shorter hospital stays, less scarring, and less post-operative pain and discomfort. Such minimally invasive techniques thus require less medication to alleviate pain associated with surgery than would be required with traditional open surgery.

Trocar assemblies, also referable to as trocars, are often used in such minimally invasive surgical procedures, such as when a port access needs to be made in a patient's abdominal walls to access an abdominal cavity. A trocar is a surgical, pen-shaped instrument including a fixed and sturdy shaft or handle and a sharp point at a closed distal end to cut through patient tissue. The trocar is often mated inside a cannula during trocar insertion through the patient's skin and underlying tissues. The trocar cuts through such skin and tissue to provide a cannula-inserted access port during surgery for other medical instruments. Such medical instruments may include, for example, endoscopes, cameras, and fiber-optic lights. However, use of conventional trocars involves a risk of trocar-related injuries to internal organs in, for example, the abdominal cavity.

Accordingly, alternative trocar assemblies and methods of use to obtain access to an abdominal cavity of a patient in a minimally invasive manner are desired.

BRIEF SUMMARY

According to the subject matter of the present disclosure, a trocar assembly may include a head disposed at a proximal end of the trocar assembly, a shaft configured to distally extend from the head and comprising an open distal end, a cutting component extending through the open distal end of the shaft at a distal end of the trocar assembly, and a retractable protection assembly. The retractable protection assembly may be configured to one of extend and retract through the open distal end of the shaft. The retractable protection assembly may be configured to extend through the open distal end of the shaft to cover the cutting component in a naturally biased position. Additionally, the retractable protection assembly may be configured to retract from the open distal end of the shaft to expose the cutting component in a compressed position during application of pressure in a proximal direction to and along a longitudinal axis of the retractable protection assembly.

In accordance with one embodiment of the present disclosure, a method of using a trocar assembly may include providing the trocar assembly that may include a head, a shaft, a cutting component, and a retractable protection assembly. The head may be disposed at a proximal end of the trocar assembly and be configured to receive pressure, the shaft may be configured to distally extend from the head and comprises an open distal end, the cutting component may extend through the open distal end of the shaft at a distal end of the trocar assembly, the retractable protection assembly may be configured to extend through the open distal end of the shaft to cover the cutting component in a naturally biased position, and the retractable protection assembly may be configured to retract from the open distal end of the shaft to expose the cutting component in a compressed position during application of pressure to the retractable protection assembly. The method may further include disposing the distal end of the trocar assembly through an already incised skin of a patient and against a fascia of the patient, applying pressure to the head of the trocar assembly in a distal direction, receiving a counter-pressure against and along a longitudinal axis of the retractable protection assembly in a proximal direction, retracting the retractable protection assembly into the compressed position such that the cutting component is exposed, cutting the fascia and underlying tissue through the cutting component that is exposed to create an access port for insertion of a cannula mated to the shaft of the trocar assembly, reaching a cavity portion such that the retractable protection assembly no longer receives the counter-pressure, and extending the retractable protection assembly into the naturally biased position such that the cutting component is covered.

In embodiments of present disclosure, a device may include a trocar that (1) exerts less pressure to puncture the abdominal wall in order to enter the body cavity to establish a port via insertion of a cannula, (2) provides a source of illumination from the initial contact of the trocar's sharp cutting blades with a patient's fascia through the establishment of the port, and/or (3) provides for a moderated and timely withdrawal and concealment of its sharp cutting blades once the blades have penetrated the abdominal wall. A reduction in a level of resistance and counter-resistance by such a device, which includes blade having a sharp tip to cut fascia, assists to prevent sudden jerking and jumping motions and an over-reaching of the device to reduce or eliminate a risk of injury to internal organs when using the device in surgical operations.

These and additional features provided by the embodiments described herein will be more fully understood in view of the following detailed description, in conjunction with the drawings.

BRIEF DESCRIPTION OF THE SEVERAL VIEWS OF THE DRAWINGS

The embodiments set forth in the drawings are illustrative and exemplary in nature and are not intended to limit the subject matter defined by the claims. The following detailed description of specific embodiments of the present disclosure can be best understood when read in conjunction with the following drawings, where like structure is indicated with like reference numerals and in which:

DETAILED DESCRIPTION

The present disclosure relates to systems and methods to use a trocar assembly including an open distal end of a shaft through which a retractable protection assembly is moveable to aid with a cutting component cutting through fascia and tissue of a patient in a minimally invasive surgical procedure, such as a laparoscopy. The retractable protection assembly may be retracted within the open distal end of the shaft of the trocar assembly such that the cutting component extends through the open distal end. The exposed cutting component cuts through the fascia and tissue until reaching a cavity to form an access port through which a cannula mated to the trocar assembly may be inserted. The cavity may be, for example, an abdominal cavity.

Figure 1:
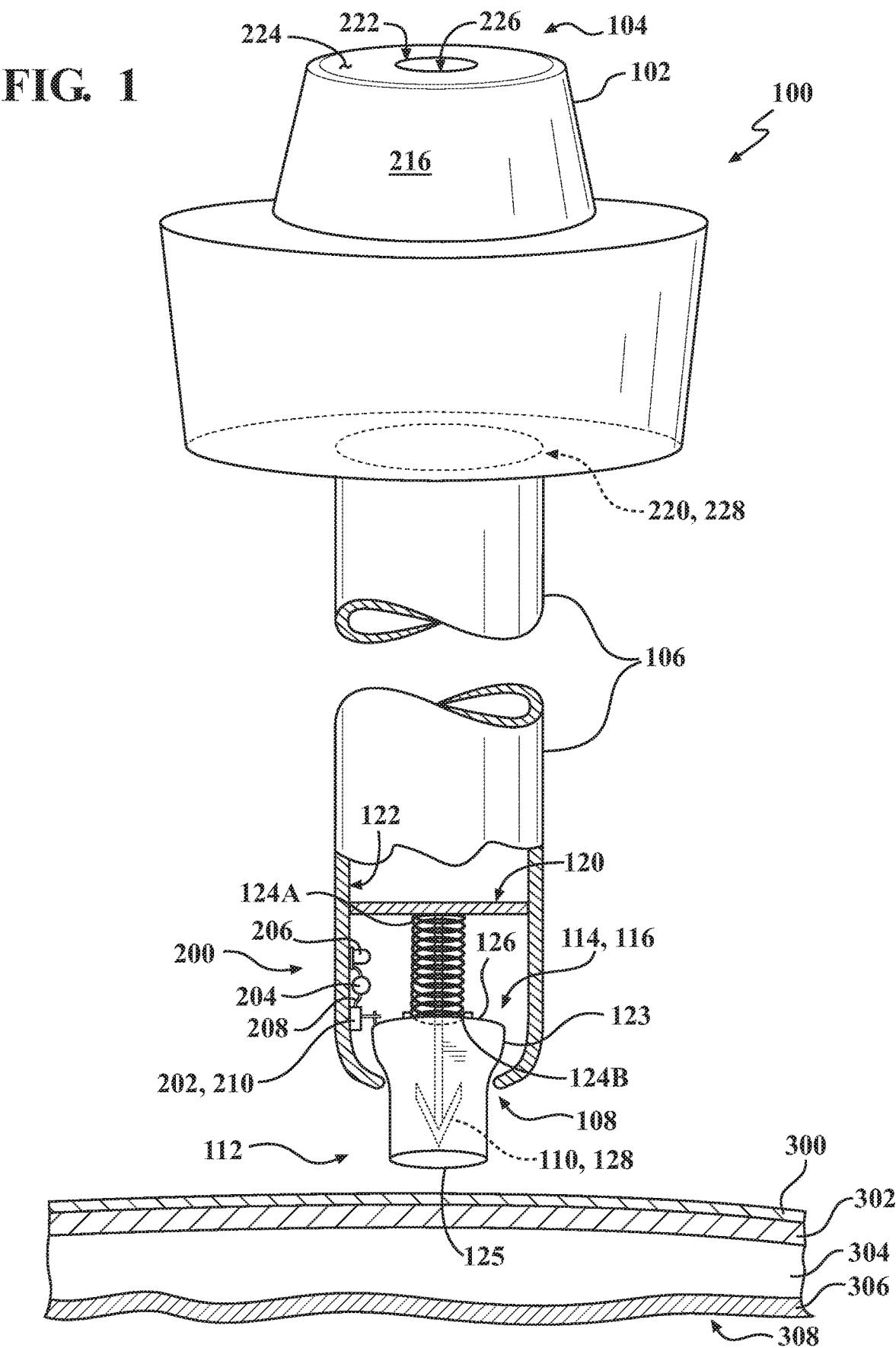
FIG. 1 illustrates an isometric view of a sheath of a trocar assembly including a cross sectional view of a distal end of the trocar assembly in a pre-insertion position in which the cone is extended to cover a cutting component, incorporating aspects of the present disclosure.

Referring initially to FIG. 1, a trocar assembly 100 includes a head 102 disposed at a proximal end 104 of the trocar assembly 100. The trocar assembly 100 further includes a shaft 106 configured to distally extend from the head 102. The shaft 106 defines an open distal end 108. As a non-limiting example, the open distal end 108 is curved inward to taper a distal end of the shaft 106 such that a retractable protection assembly 114 protruding from the open distal end 108, as described below, is prevented from falling out of the trocar assembly 100 and into, for example, an abdominal cavity 308 during a minimally invasive surgical procedure as described herein.

In embodiments, as described in greater detail below, the retractable protection assembly 114 includes a covering component 123 and a biasing element 124, wherein the covering component 123 and the biasing element 124 are coupled to be movable in combination in either a proximal direction or a distal direction, as described herein. A proximal end of the covering component 123 may have a proximal diameter that is larger than a distal diameter of the covering component 123 at a distal end. The proximal diameter of the covering component 123 may be sufficiently sized and configured such that the proximal diameter is larger than a diameter of the open distal end 108 of the shaft 106 to prevent the covering component 123 of the retractable protection assembly 114 from exiting the open distal end 108 of the shaft 106. Additionally or alternatively, the proximal end of the covering component 123 may include one or more stops as protrusions that abut against tapered walls defining the open distal end 108 of the shaft 106 to prevent the covering component 123 from exiting the open distal end 108 in operation. The distal diameter of the covering component 123 and a diameter of the biasing element 124 of the retractable protection assembly 114 may be sized and configured such that each diameter is smaller than the diameter of the open distal end 108.

Figure 2:
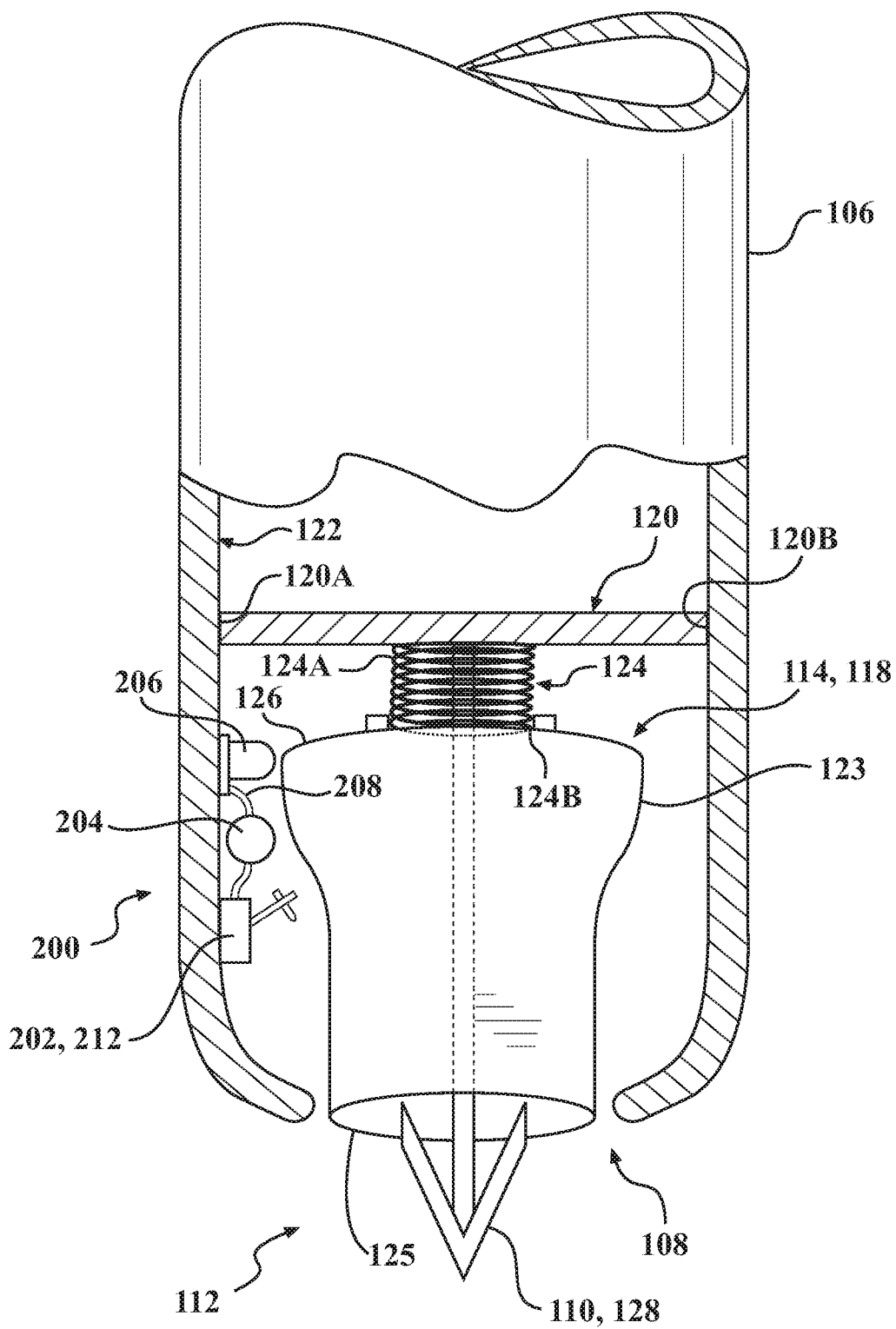
FIG. 2 is a detailed view of the distal end of the trocar assembly of FIG. 1 in an insertion position in which the cone is retracted to expose the cutting component.

As illustrated in FIGS. 1-2, the trocar assembly 100 includes a cutting component 110 extending through the open distal end 108 of the shaft 106 at a distal end 112 of the trocar assembly 100. Additionally, the trocar assembly 100 includes the retractable protection assembly 114 configured to one of extend and retract through the open distal end 108 of the shaft 106. A distal end of the retractable protection assembly 114 may include an atraumatic tip 125 at the distal end of the covering component 123 that is configured to provide a protective covering for the cutting component 110 and to not cut through the vital organs. Such an atraumatic tip 125 comprises a blunt edge that is configured to provide a protective shield with respect to solid human matter such that the blunt edge is not configured to cut through fascia, tissue, and/or vital organs. FIG. 1 illustrates a distal end of the covering component 123 that is cone-shaped and includes a proximal diameter that is larger than a distal diameter at the distal end that includes the atraumatic tip 125. For example, the proximal end of the covering component 123 may taper inwardly to an inner circumference of the covering component 123, which inner circumference may have an inner circumference diameter that is smaller than the proximal diameter of the proximal end of the covering component 123. The inner circumference may distally extend toward the distal end of the covering component 123 such that the inner circumference diameter is substantially the same as the distal diameter of the distal end of the covering component 123.

As shown in FIG. 1, the retractable protection assembly 114 including the covering component 123 and the biasing element 124 is configured to extend through the open distal end 108 of the shaft 106 to cover the cutting component 110 in a naturally biased position 116. In particular, the covering component 123 of the retractable protection assembly 114 is configured to extend through the open distal end 108 to cover the cutting component 110 in the naturally biased position 116 in which the biasing element 124 is resting and naturally biased. Further, as shown in FIG. 2, the retractable protection assembly 114 is configured to retract from the open distal end 108 of the shaft to expose the cutting component 110 in a compressed position 118 during application of pressure along a longitudinal axis of the retractable protection assembly 114 in a proximal direction. In particular, the covering component 123 of the retractable protection assembly 114 is configured to retract from the open distal end 108 to expose the cutting component 110 in the compressed position 118 in which the biasing element 124 is compressed by the covering component 123 upon application of pressure at a distal end of and along a longitudinal axis of the covering component 123 in the proximal direction.

By way of example and not as a limitation, the shaft 106 includes a divider wall 120 and an inner wall 122. The divider wall 120 is connected at respective ends 120A, 120B to the inner wall 122 of the shaft 106. The retractable protection assembly 114 includes the covering component 123 and the biasing element 124, and the covering component 123 is configured to be connected to the divider wall 120 through the biasing element 124. The biasing element 124 may include a coil spring, a helical spring, a leaf spring, or a like biasing component that is understood to be within the scope of this disclosure. A first end 124A of the biasing element 124 is fixed to the divider wall 120, and a second end 124B of the biasing element 124 is fixed to a proximal end 126 of the covering component 123. The covering component 123 of the retractable protection assembly 114 is configured to retract from the open distal end 108 to expose the cutting component 110 in the compressed position 118 in which the biasing element 124 is compressed by the covering component 123 against the divider wall 120 upon application of pressure at a distal end of and along a longitudinal axis of the covering component 123 in the proximal direction.

Figure 3:
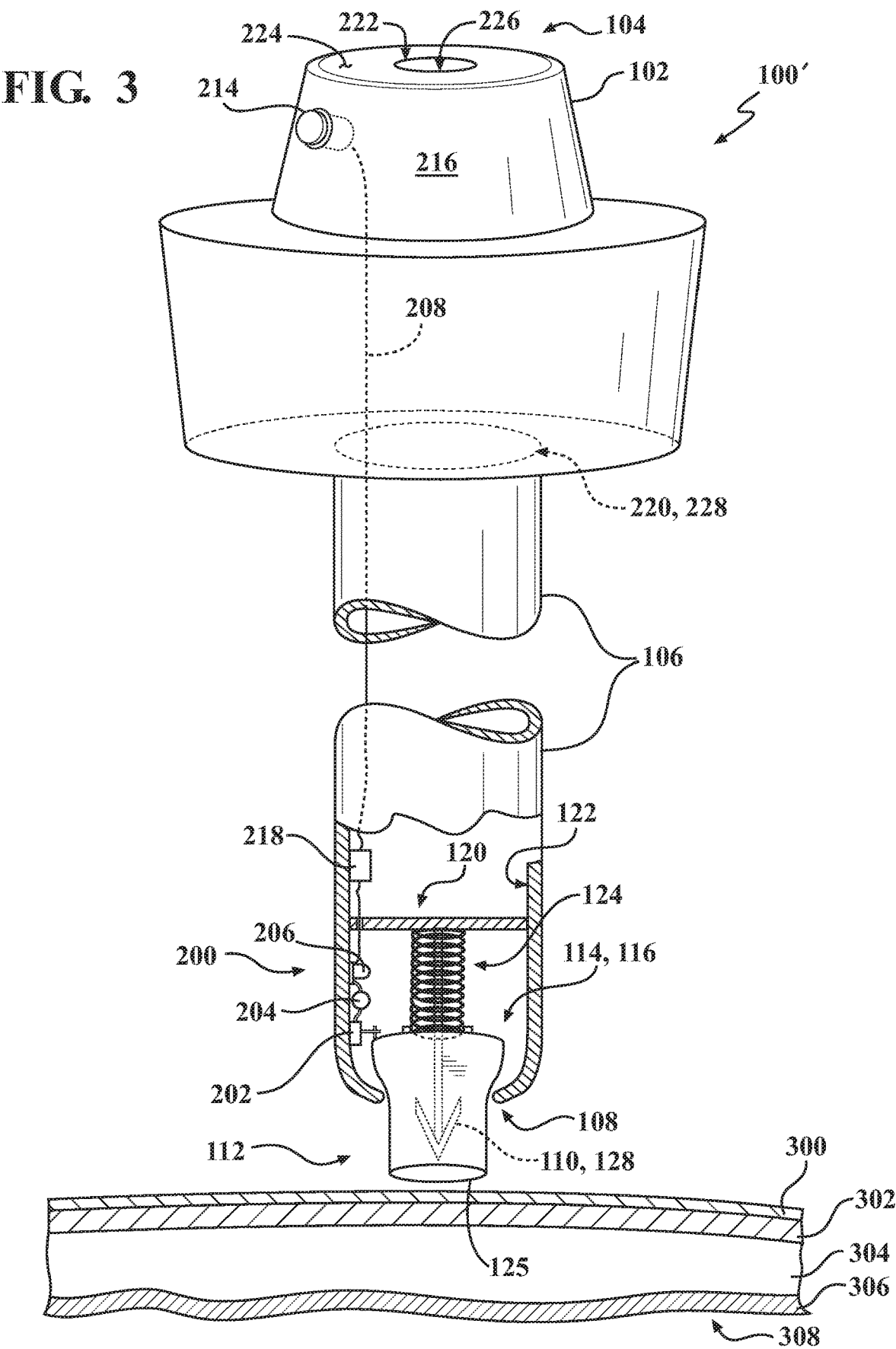
FIG. 3 illustrates an isometric view of a sheath of another trocar assembly including a manual switch and a cross sectional view of a distal end of the trocar assembly in a pre-insertion position, incorporating aspects of the present disclosure.

In an embodiment, as shown in FIGS. 1-2, the biasing element 124 is configured to be disposed around the cutting component 110. For example, the cutting component 110 distally extends from the divider wall 120 through a central portion of the biasing element 124. Further, the covering component 123 may be a cone-shape. As shown in FIGS. 1-3, the cutting component 110 comprises a knife blade 128 fixed to and distally extending from the divider wall 120, and the cone-shaped covering component 123 is configured to house the knife blade 128 when the retractable protection assembly 114 is in the naturally biased position 116. The knife blade 128 of the cutting component 110 may define an arrow-shape at a distal end.

Figure 4:
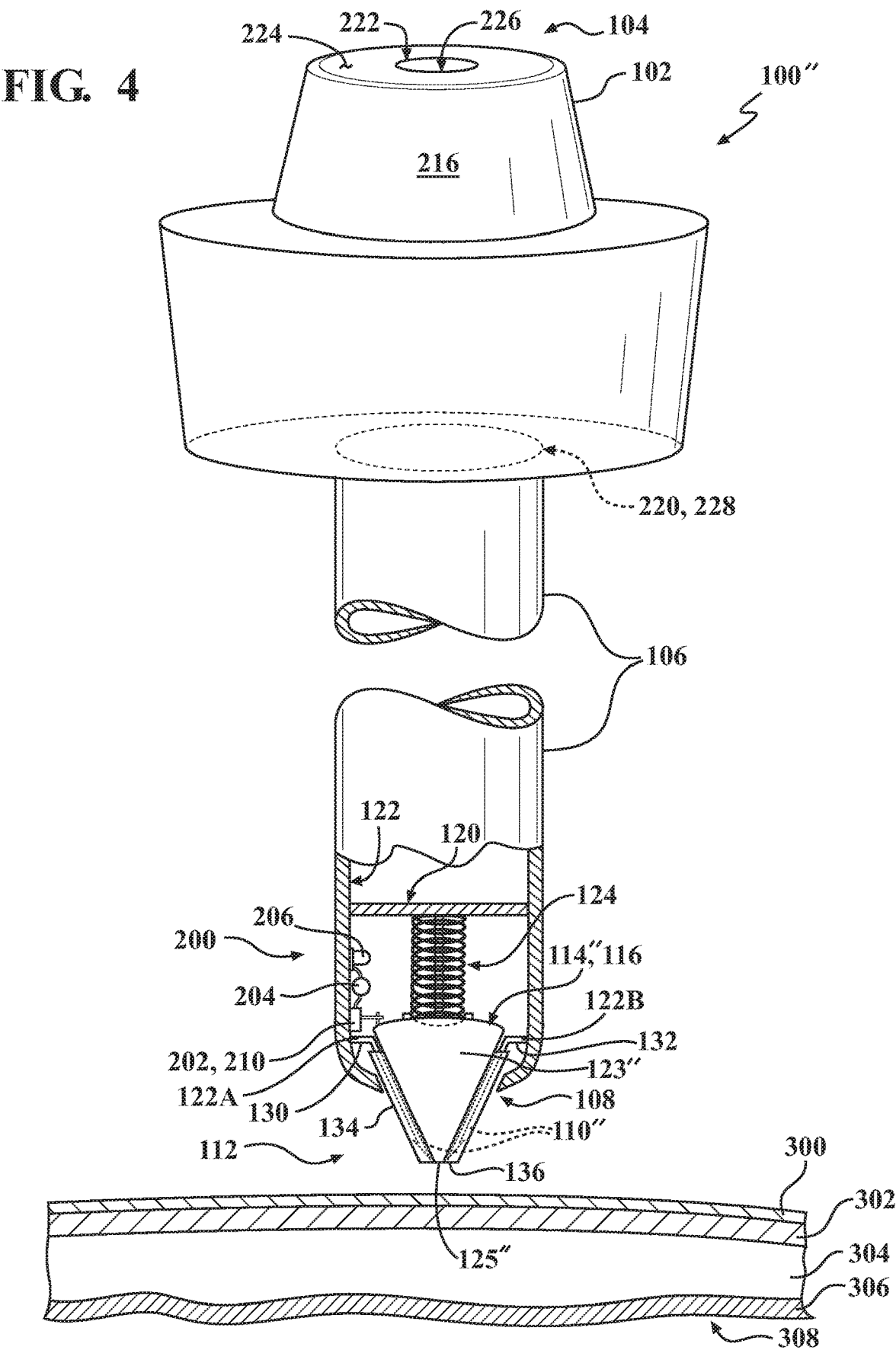
FIG. 4 illustrates an isometric view of a sheath of yet another trocar assembly including a cross sectional view of a distal end of the trocar assembly in a pre-insertion position in which the cone is extended to cover a pair of cutting features, incorporating aspects of the present disclosure.
Figure 5:
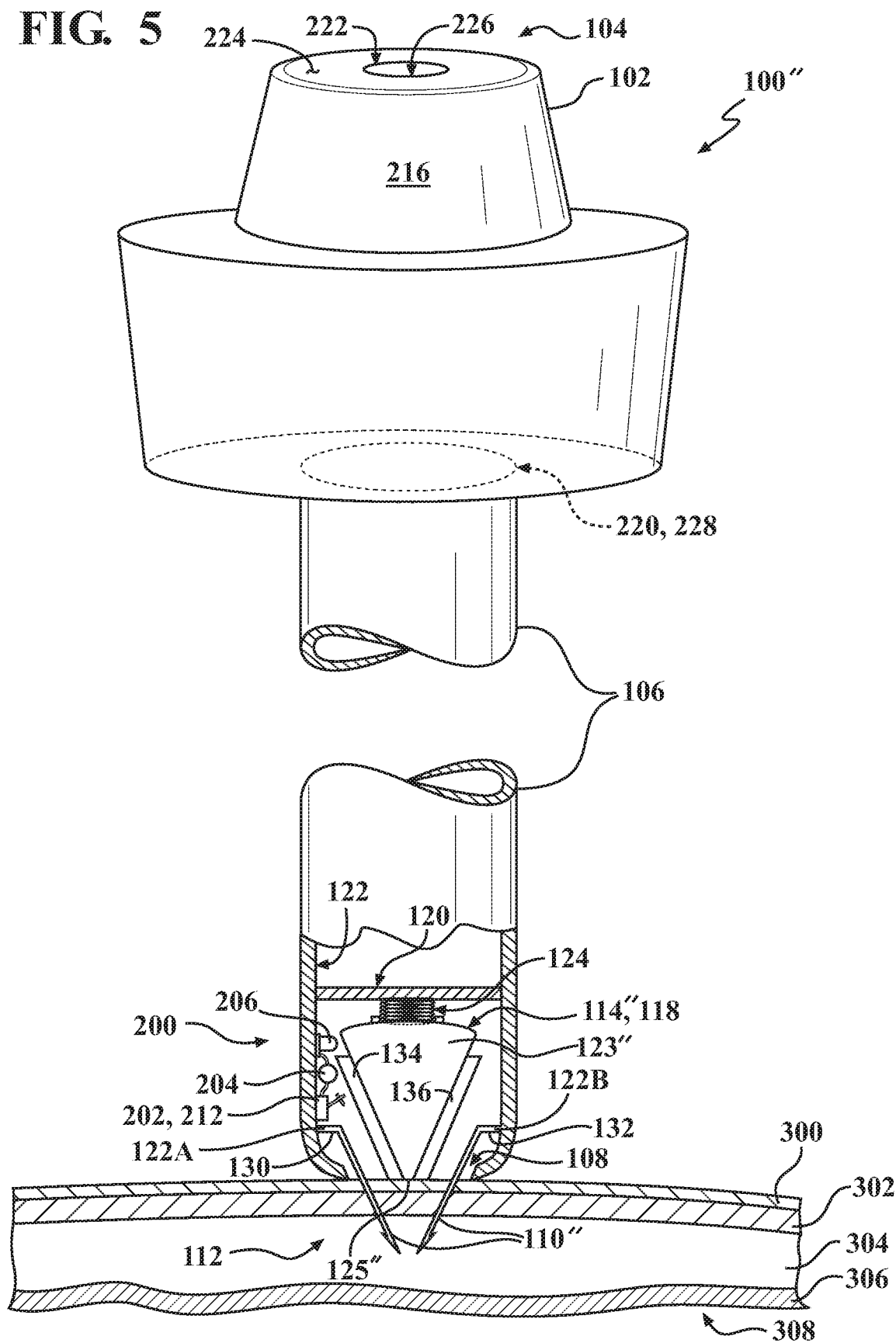
FIG. 5 is a detailed view of the distal end of the trocar assembly of FIG. 4 in an insertion position in which the cone is retracted to expose the pair of cutting features.

In an embodiment shown in FIGS. 4-5, a trocar assembly 100" is similar to the trocar assembly 100 of FIGS. 1-2 except differs with respect to a cutting component 110", a retractable protection assembly 114", and a covering component 123". For example, the cutting component 110" includes a pair of cutting features. The pair of cutting features may be, for example, a respective pair of knife blades 130, 132 fixed to and laterally extending from a pair of opposite sides 122A, 122B of the inner wall 122 to then distally extend through the open distal end 108 of the shaft 106. The pair of knife blades 130, 132 may include barbed distal ends. Further, a cone-shaped covering component 123" includes grooves 134, 136 along a pair of sidewalls of the cone-shaped covering component 123". The grooves 134, 136 are configured to house the respective pair of knife blades 130, 132 when the retractable protection assembly 114" is in the naturally biased position 116 shown in FIG. 4. The covering component 123" may further include an atraumatic tip 125" such that a distal end of the covering component 123" comprises a blunt edge that is configured to provide a protective shield with respect to solid human matter such that the blunt edge is not configured to cut through fascia, tissue, and/or vital organs. The covering component 123" may comprise a funnel, cone-shape having a proximal diameter that tapers inwardly to a distal diameter such that the distal diameter is smaller than the proximal diameter. When the retractable protection assembly 114" is in the compressed position 118 shown in FIG. 5, the pair of knife blade 130, 132 are exposed such that cutting component 110" is able to cut through fascia and tissue of a patient, for example.

In any of the embodiments described herein, the fixed cutting component 110 has a sharp-tipped knife blade 128 that is configured to cut the fascia and the soft tissue of a patient. Through the distally downwards (extended state) and the proximally upwards (retracted state) motion of the retractable protection assembly 114 at the divider wall 120, the sharp tip of the knife blade 128 is protected and/or exposed during use of the trocar assembly 100 as described herein. When a surgeon presses on the proximal head 102 of the trocar assembly 100, the retractable protection assembly moves upwards to expose the cutting component 110, which cuts the fascia and the soft tissue with a minimal exerted force because of the sharp-tip of the knife blade 128 requiring a measurably less pressure and experiencing a significant loss of resistance from the fascia against the penetrating trocar entering the body cavity such as abdominal cavity 308. When the trocar enters the abdominal cavity 308, the retractable protection assembly 114 is returned to its original position, covering and protecting the cutting component 110, which is now in its non-cutting position. Such required reduced pressure results in a reduction in an amount of sudden counter-pressure that occurs when reaching the abdominal cavity 308 (which sudden counter-pressure is experienced by most trocars having blunt tips and which are pushed through the abdominal layers). The sudden loss of counter-pressure at high pressure levels that are induced by blunt-tipped trocars result in forward jerking and jumping motions causing a loss of control of a trocar assembly by a surgeon that, in turn, produces over-reaching, which is likely to result in vital organ injuries. Therefore, a measurable reduction in a level of resistance and counter-resistance as provided by the trocar assemblies 100, 100', 100" described herein, which cut the fascia, contrary to blunt-tip trocars that push the blunt tip into layers of an abdominal wall, results in a prevention of over-reaching and the sudden jerking and jumping motions to reduce or eliminate a risk of internal organ injuries.

In embodiments, the trocar assembly further comprises a switch assembly 200. As shown in FIGS. 1-5, the switch assembly 200 may include components disposed below or above the divider wall 120 that are attached to the inner wall 122 of the shaft 106. The components may include, for example, an automatic switch 202 disposed below the divider wall 120, an electronic storage device such as a battery 204, and an illumination device 206. The automatic switch 202, the battery 204, and the illumination device 206 are in electronic communication through one or more wires 208. The illumination device may include at least one light-emitting diode (LED). The battery 204 may be an alkaline coin battery or a battery pack.

The automatic switch 202 may be configured to be in a first position 210 when the retractable protection assembly 114, 114" is in the naturally biased position 116. Further, automatic switch 202 may be configured to be in a second position 212 when the retractable protection assembly 114, 114" is in the compressed position 118 such that movement of the retractable protection assembly 114, 114" is configured to effect movement of the automatic switch 202. The first position 210 is one of an ON state and an OFF state, and the second position 212 is the other of the ON state and the OFF state. The illumination device 206 is configured to be in an illuminated state when the automatic switch 202 is in the ON state and to be in a non-illuminated state when the automatic switch 202 is in the OFF state. Thus, the LED will turn on (i.e., be in the illuminated state) when the automatic switch 202 is in the ON state and will turn off (i.e., be in the non-illuminated state) when the automatic switch 202 is in the OFF state.

In an embodiment shown in FIG. 3, the switch assembly 200 may include a manual switch 214. The manual switch 214 is shown as disposed on an outer surface 216 of the head 102 of the trocar assembly 100' of FIG. 3, which is similar to the trocar assembly 100 of FIG. 1 except for the manual switch 214 and additional, secondary electronic storage device 218. The manual switch 214 may be connected to the additional, secondary electronic storage device 218 through one or more wires 208, such as a wire 208 that extends through an aperture 226 extending from the head 102 through an open proximal end 220 of the shaft 106 and through a central opening of the shaft 106 defined by the inner wall 122 of the shaft 106.

Thus, the switch assembly 200 of the trocar assembly 100' of FIG. 3 includes the manual switch 214, the illumination device 206, and an electronic storage device including the battery 204 and the secondary electronic storage device 218. The electronic storage device, including the battery 204 and the secondary electronic storage device 218, and the illumination device 206 are disposed within the shaft 106. The battery 204 is disposed distally below the divider wall 120, and the secondary electronic storage device 218 is disposed proximally above the divider wall 120. As a non-limiting example, the secondary electronic storage device 218 includes an alkaline battery pack disposed proximally above the divider wall 120, and the illumination device 206 comprises at least one light-emitting diode (LED) disposed distally below the divider wall 120. The manual switch 214, the electronic storage device, and the illumination device 206 are in electronic communication through one or more wires 208.

The manual switch 214 is configured to switch between an ON state and an OFF state through manual compression. The LED is configured to be in an illuminated state when the manual switch 214 is in the ON state and to be in a non-illuminated state when the manual switch 214 is in the OFF state.

While the embodiment of FIG. 3 illustrate the switch assembly 200 as including the automatic switch 202 and the manual switch 214, either or both of these switches may not be included with the trocar assemblies 100, 100', 100" of the present disclosure. For example, the trocar assembly 100' of FIG. 3 may only include the manual switch 214, the secondary electronic storage device 218, and the illumination device 206 that are in electrical communication through one or more wires 208. Further, the illumination device 206 may be disposed distally below or proximally above the divider wall 120. Moreover, the switch assembly 200 may include only one of the battery 204 and the secondary electronic storage device 218.

In embodiments, the shaft 106 of the trocar assemblies 100, 100', 100" includes an open proximal end 220. The head 102 includes an open proximal end 222 that is configured to fluidly align with the open proximal end 220 of the shaft 106. Further, the head 102 defines a knob-shape and includes an outer top surface 224 defining the aperture 226 at the open proximal end 222 of the head 102. The aperture 226 extends from the open proximal end 222 of the head 102 through to an open distal end 228 of the head 102 that is generally aligned with the open proximal end 220 of the shaft 106. In alternative embodiments, such a general alignment may be fluidly aligned such that the divider wall 120 may include or define one or more apertures with respect to the shaft 106. In such embodiments, the open distal end 108 of the shaft 106 is in fluid communication with the open proximal end 220 of the shaft 106 and the aperture 226 extending between the open distal end 228 of the head 102 and the open proximal end 222 of the head 102. In alternative embodiments, the divider wall 120 fully divides a proximal space from a distal space of the shaft 106 such that the open distal end 108 of the shaft 106 is not in fluid communication with the aperture 226 of the head 102.

In embodiments, the cannula and/or trocar assembly 100, 100', 100" are made of a clear, transparent, medical-grade material. By way of example and not as a limitation, when the cannula and trocar assembly 100, 100', 100" is made of clear, transparent, translucent, and/or opaque material, a surgeon would have viewable access to the illumination device 206. At least a portion of wall of the cannula and/or trocar assembly 100, 100', 100" may be made of clear, transparent, translucent, and/or opaque material such that illumination from the illumination device 206 is viewable by a surgeon. For example, the cannula and/or trocar assembly 100, 100', 100" may include at least a transparent or translucent portion comprising a transparent or translucent material such that the illumination device 206 is disposed adjacent to the transparent or translucent portion. In such embodiments, whether or not the divider wall 120 permits fluid communication between the head 102 and the open distal end 108, a surgeon would be able to see whether the illumination device 206 is illuminated as described herein. As an example, in one embodiment as described herein, the illumination device 206 is illuminated when the retractable protection assembly 114, 114" is in the compression position 118. However, if the divider wall 120 includes one or more apertures to permit fluid communication between the aperture 226 of the head 102 and the open distal end 108 of the shaft 106, illumination from the illumination device 206 may additionally or alternatively be viewed from the aperture 226, whether or not the cannula and/or trocar assembly 100, 100', 100" are made of a clear, transparent, medical-grade material.

The trocar assemblies 100, 100', 100' may be employed in one or more methods of use with respect to a patient during minimally invasive surgery, for example. By way of example and not as a limitation, a method of using a trocar assembly 100, 100', 100" includes providing the trocar assembly 100, 100', 100" that comprise the head 102, the shaft 106, a cutting component 110, 110", and a retractable protection assembly 114, 114" as described above. For example, the head 102 is disposed at the proximal end 104 of the trocar assembly 100, 100', 100" and is configured to receive pressure, and the shaft 106 is configured to distally extend from the head 102 and comprises the open distal end 108. The cutting component 110, 110" extends through the open distal end 108 of the shaft 106 at a distal end 112 of the trocar assembly 100, 100', 100". The retractable protection assembly 114, 114" is configured to extend through the open distal end 108 of the shaft 106 to respectively cover the cutting component 110, 110" in the naturally biased position 116. Further, the retractable protection assembly 114, 114" is configured to retract from the open distal end 108 of the shaft 106 to expose the respective cutting component 110, 110" in the compressed position 118 during application of pressure to the retractable protection assembly 114, 114".

The method includes disposing the distal end 112 of the trocar assembly 100, 100', 100" against an already incised first layer of skin of a patient. For example, the first layer may be an already incised skin layer 300. The skin layer 300 may include the soft outer tissue comprising skin of a patient, subcutaneous tissue underlying the skin, and fascia comprising a connective tissue sheet underlying the subcutaneous tissue. Thus, the method may include disposing the distal end 112 of the trocar assembly 100, 100', 100" through an already incised skin 300 of a patient and against a fascia 304 to cut the fascia 304 of the patient.

A surgeon, for example, may apply pressure to the head 102 of the trocar assembly 100, 100', 100" in a distal direction such that a counter-pressure is received against the retractable protection assembly 114, 114" in a proximal direction opposite the distal direction when the distal end 112 of the trocar assembly 100, 100', 100" is pressed against the already incised skin layer 300. Further, upon this counter-pressure, the retractable protection assembly 114, 114" is retracted from the naturally biased position 116 into the compressed position 118 such that the respective cutting component 110, 110" is exposed as described herein.

The trocar assembly 100, 100', 100" may then proceed to cut through the fascia and through the underlying tissue that is exposed to create an access port for insertion of a cannula that is mated to the shaft 106 of the trocar assembly 100, 100', 100". For example, the cutting component 110, 110" cuts through the underlying fascia transversalis 304 disposed between the muscle 302 and the peritoneum 306 lining the abdominal cavity 308, and through the peritoneum 306 to reach the abdominal cavity 308. The retractable protection assembly 114, 114" no longer receives the counter-pressure when the abdominal cavity 308 is reached such that the retractable protection assembly 114, 114" springs and extends back into the naturally biased position 116, in which position the respective cutting component 110, 110" is no longer exposed and instead is covered as described herein. The trocar assembly 100, 100', 100" may then be removed from the patient, and the cannula may be retained in an inserted position at the created access port.

In embodiments including an automatic switch 202 as described herein, the method may further include compressing the retractable protection assembly 114, 114" against the divider wall 120 through the biasing element 124 that connects the retractable protection assembly 114, 114" to the divider wall 120 when receiving the counter-pressure against the retractable protection assembly 114, 114" such that the automatic switch 202 switches from the first position 210 to the second position 212. Thus, the automatic switch 202 switches from the first position 210 to the second position 212 based on movement of the retractable protection assembly 114, 114" as the biasing element 124 transitions between the naturally biased position 116 and the compressed position 118 along with the retractable protection assembly 114, 114". As described above, the first position 210 is one of an ON state and an OFF state, and the second position 212 is the other of the ON state and the OFF state, and the illumination device comprises a light-emitting diode (LED). Thus, the method includes illuminating the LED when the automatic switch is in the ON state, and turning off the LED when the automatic switch is in the OFF state. Therefore, when the first position 210 is an ON state, the second position 212 is an OFF state such that when the biasing element 124 transitions between the naturally biased position 116 and the compressed position 118 along with the retractable protection assembly 114, 114", the automatic switch 202 switches from the ON state to the OFF state as the LED turns from ON (i.e., illuminated) to OFF (i.e., not illuminated). However, when the first position 210 is an OFF state, the second position 212 is an ON state such that when the biasing element 124 transitions between the naturally biased position 116 and the compressed position 118 along with the retractable protection assembly 114, 114", the automatic switch 202 switches from the OFF state to the ON state as the LED turns from OFF (i.e., not illuminated) to ON (i.e., illuminated).

In embodiments including a manual switch 214 as described herein, the method may further include pressing the manual switch 214 to transition the manual switch 214 from a first state to a second state. The first state is one of an ON state and an OFF state, and the second state is the other of the ON state and the OFF state. The method may include illuminating the LED when the manual switch 214 is in the ON state and turning off the LED when the manual switch 214 is in the OFF state.

The trocar assemblies 100, 100', 100" may be mated with a clear, transparent, and/or translucent cannula to enhance visualization during an initial insertion of the trocar assembly 100, 100', 100" into the fascia of a patient to create the access port for the cannula as described herein. A cutting motion of the cutting components 110, 110" as described herein along with the retractable protection assembly 114, 114" configuration provides for less exertion of pressure to a head of the trocar assembly than with trocar assemblies including a closed distal end, for example. Less pressure reduces the forward jerking and jumping motions that may otherwise occur through a sudden counter pressure upon reaching an abdominal cavity after application of a high pressure against the head of the trocar assembly. Such forward jerking and jumping motions may result in an increase in potential injuries to vital organs. Thus, when using a trocar assembly to create the access port, use of the trocar assemblies with the open distal end as described herein reduces such forward jerking and jumping motions, increases user control with respect to the trocar assembly, and reduces a risk of injury to such vital organs. The trocar assemblies described herein exert less pressure to puncture an abdominal wall to enter the abdominal cavity to establish the access port within which to insert the cannula. Further, the trocar assemblies described herein may provide a source of illumination from an initial contact of the cutting components 110, 110" through activation of the automatic switch 202 to illuminate a light source such as the illumination device 206. For example, when the respective retractable protection assembly 114, 114" transitions from a naturally biased position 116 in which the respective cutting component 110, 110" is covered to a compressed position 118 in which the respective cutting component 110, 110" is exposed for cutting, the automatic switch 202 may correspondingly transition from an OFF position to an ON position in which the illumination device 206 is illuminated and turned on.

Once abdominal cavity 308 is reached, the respective retractable protection assembly 114, 114" transitions back to the naturally biased position 116 to cover the respective cutting component 110, 110" and protect vital organs from the blades when the distal end 112 of the trocar assembly 100, 100' 100" is disposed within the abdominal cavity 308. The automatic switch 202 may stay in the ON position even after the abdominal cavity 308 has been reached and may be turned off through, for example, use of a manual switch 214 as described herein. In other embodiments, the automatic switch 202 may correspondingly transition when the abdominal cavity 308 is reached from the ON position to the OFF position in which the illumination device 206 is turned off indicating the abdominal cavity 308 has been reached. For example, the automatic switch 202 may include a switch assembly and configuration as described in U.S. Pat. No. 8,838,206 to the present inventor, issued Sep. 16, 2014, and which is incorporated by its entirety herein. In embodiments, a reset feature may be used to manually reset the automatic switch 202 into a desired position.

Figure 6:
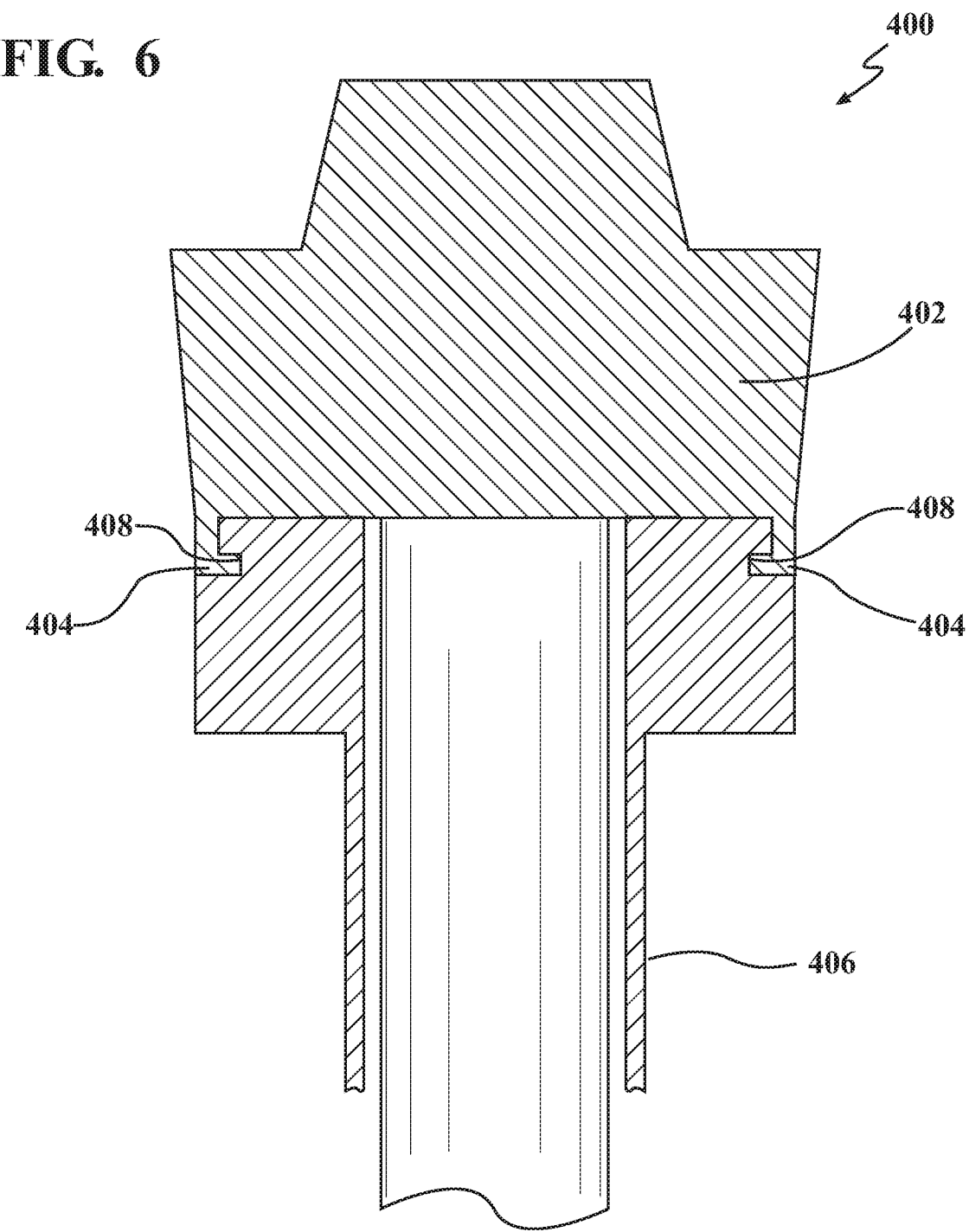
FIG. 6 illustrates an isometric view of a distal section of a proximal head of a trocar assembly including locking component(s) to couple with corresponding locking component(s) of a proximal end of a cannula, incorporating aspects of the present disclosure.

In embodiments, the trocar assemblies 100, 100', 100" may include one or more locking components to couple and releasably lock with one or more corresponding locking components of a mating cannula. Referring to FIG. 6, and as a non-limiting example, a trocar assembly 400 includes a trocar 402 having one or more locking components 404 and a cannula 406 having a corresponding set of one or more locking components 408. The one or more locking components 408 of the cannula 406 are configured to releasably couple and lock with the one or more locking components 404 of the trocar 402. The one or more locking components 404 of the trocar 402 may comprise walls defining one of a protrusion or notch and the one or more locking components 408 of the cannula 406 may comprise walls defining the other of the protrusion or notch. For example, the one or more locking components 404 of the trocar 402 may comprise walls defining a notch and the one or more locking components 408 of the cannula 406 may comprise walls defining a protrusion configured to be received by the notch. Alternatively, the one or more locking components 404 of the trocar 402 may comprise walls defining a protrusion and the one or more locking components 408 of the cannula 406 may comprise walls defining a notch configured to receive the protrusion.

In an embodiment, the one or more locking components 404 of the trocar 402 may comprise walls defining a pair of protrusions at opposite ends extending distally below outer ends of a head of the trocar 402 that define an L-shape including a distally extending wall as a side portion and an internally extending distal wall as a bottom portion. The one or more locking components 408 of the cannula 406 may comprise walls defining a corresponding pair of notches at a proximal end of the cannula defining a reverse L-shape configured to receive the pair of protrusions. For example, the reverse L-shape may include an outwardly extending proximal wall and a distally extending inner wall spaced inwardly of the outwardly extending proximal wall. Each outwardly extending proximal wall of the pair of notches of the locking components 408 of the cannula 406 is configured to twist to abut against each distally extending wall of the pair of protrusions of the locking components 404 of the trocar 402. Further, each distally extending inner wall of the pair of notches of the locking components 408 of the cannula 406 is configured to correspondingly twist to abut against each internally extending distal wall of the pair of protrusions of the locking components 404 of the trocar 402.

In operation, a surgeon inserts the trocar 402 onto the cannula 406 such that the distal end of a proximal head of the trocar 402 forms a contact area with a proximal end of the cannula 406 to align and to engage the respective locking mechanism of each device in order to stabilize the interlocking of the two devices during use. The surgeon may then twist the trocar 402 in a first direction, such as clockwise, such that the one or more locking components 404 of the trocar 402 including L-shaped protrusions are received in the one or more locking components 408 of the cannula 406 including reverse L-shaped notches to secure the connection of the trocar 402 to the cannula 406. Such a locking connection between the trocar 402 and the cannula 406 assist to secure and stabilize the mating of the cannula 406 to the trocar 402 when both are engaged in the creation of an access port as described herein. Further, the surgeon may easily disengage the trocar 402 from the cannula 406 through twisting the trocar 402 in a second direction opposite the first direction, such as counter-clockwise, to disengage the locking components 404 from the locking components 408.

The trocar assemblies described herein minimize risks of puncturing vital organs during minimally invasive surgery and provide for enhanced visualization to more quickly and precisely establish the access port for the cannula within a body cavity of the patient.

The trocar assemblies described herein may also be disposable after a single use. Further, the trocar assemblies described herein may reduce manufacturing complexity and difficulty, provide for ease of operator use, and may provide cost-savings with respect to the trocar assemblies.

For the purposes of describing and defining the present invention, it is noted that reference herein to a variable being a "function" of (or "based on") a parameter or another variable is not intended to denote that the variable is exclusively a function of or based on the listed parameter or variable. Rather, reference herein to a variable that is a "function" of or "based on" a listed parameter is intended to be open ended such that the variable may be a function of a single parameter or a plurality of parameters.

It is also noted that recitations herein of "at least one" component, element, etc., should not be used to create an inference that the alternative use of the articles "a" or "an" should be limited to a single component, element, etc.

It is noted that recitations herein of a component of the present disclosure being "configured" or "programmed" in a particular way, to embody a particular property, or to function in a particular manner, are structural recitations, as opposed to recitations of intended use. More specifically, the references herein to the manner in which a component is "configured" or "programmed" denotes an existing physical condition of the component and, as such, is to be taken as a definite recitation of the structural characteristics of the component.

It is noted that terms like "preferably," "commonly," and "typically," when utilized herein, are not utilized to limit the scope of the claimed invention or to imply that certain features are critical, essential, or even important to the structure or function of the claimed invention. Rather, these terms are merely intended to identify particular aspects of an embodiment of the present disclosure or to emphasize alternative or additional features that may or may not be utilized in a particular embodiment of the present disclosure.

For the purposes of describing and defining the present invention it is noted that the terms "substantially" and "approximately" are utilized herein to represent the inherent degree of uncertainty that may be attributed to any quantitative comparison, value, measurement, or other representation. The terms "substantially" and "approximately" are also utilized herein to represent the degree by which a quantitative representation may vary from a stated reference without resulting in a change in the basic function of the subject matter at issue.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure are identified herein as preferred or particularly advantageous, it is contemplated that the present disclosure is not necessarily limited to these aspects.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

What is claimed is:

1. A trocar assembly comprising:
a head disposed at a proximal end of the trocar assembly;
a shaft configured to distally extend from the head and comprising an open distal end, an open proximal end, and an inner wall extending between the open distal end and the open proximal end and respectively comprising an inner wall distal portion and an inner wall proximal portion;
the shaft comprises a divider wall, the divider wall connected at respective ends to the inner wall of the shaft to separate the inner wall proximal portion from the inner wall distal portion, the divider wall comprising a proximal surface facing toward the inner wall proximal portion and a distal surface opposite the proximal surface and facing toward the inner wall distal portion;
a cutting component extending through the open distal end of the shaft at a distal end of the trocar assembly; and
a retractable protection assembly configured to one of extend and retract through the open distal end of the shaft, wherein the retractable protection assembly is configured to extend through the open distal end of the shaft to cover the cutting component in a naturally biased position, and the retractable protection assembly is configured to retract from the open distal end of the shaft to expose the cutting component in a compressed position during application of pressure in a proximal direction to and along a longitudinal axis of the retractable protection assembly, and the retractable protection assembly comprises a covering component configured to be connected to the divider wall through a biasing element.

2. The trocar assembly of claim 1, wherein the biasing element is a coil spring configured to be disposed around the cutting component, the cutting component comprises a knife blade comprising a proximal end fixed to the distal surface of the divider wall and distally extending from the divider wall, and the covering component is configured to house the knife blade when the retractable protection assembly is in the naturally biased position.

3. The trocar assembly of claim 1, wherein the cutting component comprises a respective pair of knife blades fixed to and laterally extending from a pair of opposite sides of the inner wall to distally extend through the open distal end of the shaft, and the covering component comprises grooves along a pair of sidewalls of the covering component configured to house the respective pair of knife blades when the retractable protection assembly is in the naturally biased position.

4. The trocar assembly of claim 1, wherein the trocar assembly further comprises:
a pair of locking components of the trocar assembly, and
a cannula comprising a pair of locking components of the cannula defined in an outer periphery of the cannula, the pair of locking components of the trocar assembly configured to extend distally below outer ends along an outer periphery of the head of the trocar assembly to releasably couple to the pair of locking components of the cannula through a twist motion.

5. The trocar assembly of claim 1, wherein:
the trocar assembly further comprises a switch assembly.

6. The trocar assembly of claim 5, wherein the switch assembly is disposed distally below the divider wall and is attached to the inner wall of the shaft and comprises an automatic switch, an electronic storage device, and an illumination device, and the automatic switch, the electronic storage device, and the illumination device are in electronic communication through one or more wires.

7. The trocar assembly of claim 6, wherein the automatic switch is configured to be in a first position when the retractable protection assembly is in the naturally biased position and to be in a second position when the retractable protection assembly is in the compressed position such that movement of the retractable protection assembly is configured to effect movement of the automatic switch.

8. The trocar assembly of claim 7, wherein:
the first position is one of an ON state and an OFF state, and the second position is the other of the ON state and the OFF state;
the illumination device comprises a light-emitting diode (LED);
the LED is configured to be in an illuminated state when the automatic switch is in the ON state; and
the LED is configured to be in a non-illuminated state when the automatic switch is in the OFF state.

9. The trocar assembly of claim 5, wherein the switch assembly comprises a manual switch disposed on an outer surface of the head of the trocar assembly, an electronic storage device, and an illumination device, the electronic storage device and the illumination device disposed within the shaft, and the manual switch, the electronic storage device, and the illumination device are in electronic communication through one or more wires.

10. The trocar assembly of claim 9, wherein the electronic storage device comprises a battery and a secondary electronic storage device, and the battery disposed below or above the divider wall.

11. The trocar assembly of claim 10, wherein the secondary electronic storage device comprises an alkaline battery pack disposed above the divider wall, and the illumination device comprises at least one light-emitting diode (LED) disposed below the divider wall.

12. The trocar assembly of claim 11, wherein the manual switch is configured to switch between an ON state and an OFF state through manual compression, and the LED is configured to be in an illuminated state when the manual switch is in the ON state and to be in a non-illuminated state when the manual switch is in the OFF state.

13. The trocar assembly of claim 10, wherein:
the switch assembly further comprises an automatic switch disposed below the divider wall,
the battery comprises an alkaline coin battery or a battery pack,
the automatic switch and the battery are in electrical communication with the LED, and
movement of the retractable protection assembly is configured to effect movement of the automatic switch such that the LED is configured to be in an illuminated state when the automatic switch is in an ON state, and the LED is configured to be in a non-illuminated state when the automatic switch is in an OFF state.

14. A method of using a trocar assembly, comprising:
providing the trocar assembly comprising a head, a shaft, a cutting component, and a retractable protection assembly, wherein:
the head is disposed at a proximal end of the trocar assembly and is configured to receive pressure,
the shaft is configured to distally extend from the head and comprises an open distal end, an open proximal end, and an inner wall extending between the open distal end and the open proximal end and respectively comprising an inner wall distal portion and an inner wall proximal portion, the shaft comprises a divider wall, the divider wall connected at respective ends to the inner wall of the shaft to separate the inner wall proximal portion from the inner wall distal portion, the divider wall comprising a proximal surface facing toward the inner wall proximal portion and a distal surface opposite the proximal surface and facing toward the inner wall distal portion, the cutting component extends through the open distal end of the shaft at a distal end of the trocar assembly, the retractable protection assembly is configured to extend through the open distal end of the shaft to cover the cutting component in a naturally biased position, and the retractable protection assembly is configured to retract from the open distal end of the shaft to expose the cutting component in a compressed position during application of pressure to the retractable protection assembly, and the retractable protection assembly comprises a covering component configured to be connected to the divider wall through a biasing element;

disposing the distal end of the trocar assembly through an already incised skin of a patient and against a fascia of the patient;

applying pressure to the head of the trocar assembly in a distal direction;

receiving a counter-pressure against and along a longitudinal axis of the retractable protection assembly in a proximal direction;

retracting the retractable protection assembly into the compressed position such that the cutting component is exposed;

cutting the fascia and underlying tissue through the cutting component that is exposed to create an access port for insertion of a cannula mated to the shaft of the trocar assembly;

reaching a cavity portion such that the retractable protection assembly no longer receives the counter-pressure; and extending the retractable protection assembly into the naturally biased position such that the cutting component is covered.

15. The method of claim 14, wherein the trocar assembly further comprises:

at least a transparent or translucent portion comprises a transparent or translucent material, and a switch assembly disposed below the divider wall of the shaft and attached to the inner wall of the shaft, the switch assembly comprising an automatic switch, an electronic storage device, and an illumination device, and the automatic switch, wherein:

the electronic storage device, and the illumination device are in electronic communication through one or more wires, and the illumination device is disposed adjacent to the transparent or translucent portion of the trocar assembly.

16. The method of claim 15, further comprising:

compressing the retractable protection assembly against the divider wall through the biasing element connecting the retractable protection assembly to the divider wall when receiving the counter-pressure against the retractable protection assembly, and switching the automatic switch from a first position to a second position based on movement of the retractable protection assembly as the biasing element transitions between the naturally biased position and the compressed position.

17. The method of claim 16, wherein the first position is one of an ON state and an OFF state, and the second position is the other of the ON state and the OFF state, and the illumination device comprises a light-emitting diode (LED), further comprising:

illuminating the LED when the automatic switch is in the ON state, and turning off the LED when the automatic switch is in the OFF state.

18. The method of claim 14, wherein the trocar assembly further comprises a switch assembly comprising a manual switch, an electronic storage device, and a light-emitting diode (LED) in electrical communication via one or more wires, the LED disposed below the divider wall of the shaft and attached to the inner wall of the shaft.

19. The method of claim 18, further comprising:

pressing the manual switch to transition the manual switch from a first state to a second state, wherein the first state is one of an ON state and an OFF state, and the second state is the other of the ON state and the OFF state;

illuminating the LED when the manual switch is in the ON state, and turning off the LED when the manual switch is in the OFF state.

* * * * *